United States Patent [19]

Altobelli et al.

[11] Patent Number: 5,002,076

[45] Date of Patent: Mar. 26, 1991

[54] HAIR TREATMENT COMPOSITION AND METHOD

[75] Inventors: Rocco F. Altobelli, Eagan; Wallace R. Hlavac; Richard J. Hudavoni, both of Minneapolis, all of Minn.

[73] Assignees: Altobella Hair Products, Inc., St. Paul; Tiro Industries, Inc., Minneapolis, both of Minn.

[21] Appl. No.: 408,604

[22] Filed: Sep. 18, 1989

Related U.S. Application Data

[62] Division of Ser. No. 178,320, Apr. 6, 1988, Pat. No. 4,913,898.

[51] Int. Cl.$^5$ .............................................. A45D 7/06
[52] U.S. Cl. ..................................... 132/206; 132/202
[58] Field of Search ............... 132/202, 203, 206, 211, 132/205

[56] References Cited

U.S. PATENT DOCUMENTS

| | | | |
|---|---|---|---|
| 1,668,608 | 5/1928 | Schnell | 132/202 |
| 2,056,358 | 10/1936 | Malone | 132/203 |
| 2,154,924 | 4/1939 | Wilson et al. | 132/206 |
| 2,817,342 | 12/1957 | Henkin | 132/203 |
| 2,948,656 | 8/1960 | Tousignant et al. | 132/203 |
| 3,693,633 | 9/1972 | Kalopissis et al. | 132/306 |
| 4,115,549 | 9/1978 | Scott | 132/303 |
| 4,237,910 | 12/1980 | Khahil et al. | 132/202 |
| 4,545,978 | 10/1985 | Kalopissis et al. | 424/10 |
| 4,610,261 | 9/1986 | Madrange et al. | 132/206 |
| 4,637,933 | 1/1987 | Zabotto nee Arribau et al. | 424/131 |
| 4,844,888 | 7/1989 | Zawadzki | 132/203 |

FOREIGN PATENT DOCUMENTS 55-139314  4/1979  Japan .

*Primary Examiner*—Paul J. Hirsch
*Attorney, Agent, or Firm*—Merchant, Gould, Smith, Edell, Welter & Schmidt

[57] ABSTRACT

A method for treating hair with an aqueous clay-based conditioning composition that involves applying the composition to hair and exposing the hair to heat for a period of time sufficient to dry the composition to a hard and flaky state. The conditioning composition includes effective amounts of a reconstruction component (protein), a moisturizer component having hyaluronic acid and a shine imparting component having henna extract.

7 Claims, No Drawings

HAIR TREATMENT COMPOSITION AND METHOD

This is a division, of application Ser. No. 07/178,320, filed Apr. 6, 1988, now U.S. Pat. No. 4,913,898.

FIELD OF THE INVENTION

This invention relates to aqueous clay-based hair treatment compositions including a reconstruction component, a shine imparting component and a moisturizing component that can be used in a single application to condition hair.

BACKGROUND OF THE INVENTION

A variety of chemical preparation are available and commonly used to change the natural characteristics of hair. Color and style are typically changed using dyes, bleaches and permanent-waving preparations. These chemical preparations can damage hair.

In general, hair has a filamentous structure with an inner component referred to as the cortex and an outer flap-like component referred to as the cuticle. In the natural state, the cuticle is closed providing natural elasticity. When the cuticle is open, this natural elasticity is lost. Hair damaged by chemical preparations, in many cases, exhibits open cuticles. For example, use of dye mixtures can dry hair resulting in loss of elasticity and body.

To restore desired elasticity and body to hair following use of chemical preparations, hair conditioning treatments are commonly employed. Typical hair conditioning treatments involve the use of a number of components to restore hair qualities lost during chemical treatment. To reconstruct the hair and bring back elasticity a protein pack is commonly employed. Also, a component such as henna can be applied to the hair to impart shine or luster. Another typical post-treatment conditioning component is a moisturizer which is used to enhance the body of hair.

While hair treatments that reconstruct, add shine, and moisturize hair are known, these treatments are both time consuming and labor intensive. Specifically, each component in the hair conditioning process must be separately applied and removed. The application of a protein pack typically requires 10 to 20 minutes and must then be removed prior to applying further conditioning components. Treatment of hair with a shine imparting component such as henna can involve up to one hour. The shine imparting component must also be removed before another conditioning preparation, such as a moisturizer is used. In the case of a three part hair conditioning treatment, to reconstruct, impart shine and moisturize hair, separate application and removal of each component requires a total treatment time of about 1 to 1½ hours. It is to be understood that this 1 to 1½ hour process is in addition to whatever time is involved in the particular dye or permanent-waving treatment which precedes the hair conditioning procedure.

Accordingly, a substantial need exists for a hair conditioning composition containing a reconstruction component, a shine imparting component and a moisturizing component that can be employed in a single application procedure of short duration.

SUMMARY OF THE INVENTION

The present invention provides a hair treatment composition in the form of an aqueous clay-based paste which includes effective amounts of a reconstruction component, a shine imparting component and a moisturizing component. We have found that the composition is useful in a method to condition hair involving: applying the preparation to hair; and exposing the prepared hair to heat until the preparation dries to a hard and flaky state. The dried pack is then solubilized and removed with a commercially available cleansing shampoo.

In a preferred embodiment, the method of use of the hair treatment composition involves a two step heat treatment. In the first step, the prepared hair is enclosed in a cover means such as a cap. In the second heat step, which is of shorter duration than the first, the prepared hair is uncovered and exposed directly to heat.

The hair treatment composition and method of use of the present invention exhibits a number of advantages. First, the present invention eliminates the need for multiple step conditioning treatments which involve separate application and removal of conditioning components. The present invention provides a composition that can be used in a single application to condition hair by reconstructing damaged hair together with adding shine and body. Second, in contrast to the existing multiple step conditioning treatments, which require from about 1 hour to 1½ hours, the method of the present requires only about 20 to 40 minutes. Third, the present invention is labor saving in that one application step is required, thereby enabling more efficient use of beauty salon personnel.

The moisturizer hyaluronic acid penetrates deeply; while clay locks in moisture and protein, naturally sealing the cuticle layer. The present composition conditions, seals and enhances natural sheen and a light but full appearance on hair.

DETAILED DESCRIPTION OF THE INVENTION

The present hair conditioning compositions as preferably formulated include a sufficient amount of a clay component to form a malleable paste having an oil phase and water, together with effective amounts of a reconstruction component, a shine imparting component and a moisturizing component. The desired paste consistency of the composition is achieved and maintained with the aid of cationic, nonionic and anionic polymers, surfactants and emulsifiers.

The present paste is an aqueous clay-based composition. Aqueous clay-based composition refers to a paste incorporating water and clay in amounts sufficient to form a dry and flaky coating on hair when subjected to heat as described herein. Preferably, the paste has the consistency of a light modeling clay. In a preferred embodiment, from about 15-25% of the composition is clay. In general, clay refers to a composition of extremely fine crystals or particles of rock which in many cases has the characteristic of plasticity. The very fine particles yield a very large specific surface that is physically sorptive and chemically surface-reactive.

The present compositions can employ a number of clays either alone or in combination. For example, kaolin, fuller's earth, montmorillonite, georgia or calcine clays can be used. Preferred compositions employ a combination of kaolin and fuller's earth. More preferably, the clay of the present composition is from about 13-20% kaolin available from Georgian Kaolin as Hydride Flat D and about 2-12% fuller's earth is preferred, one of skill in the art will be able to use other types of clays based on an evaluation of the hydration, emulsion lattice filling characteristics, and thixotropic and rhelogic properties of the preferred compositions described herein.

The present paste will incorporate an effective amount of reconstruction component in the form of protein. Preferably, the composition will include from about 2-20% substantive protein. Most preferably, the composition will include at least 10% protein having average molecular weights ranging from 1,000 to 5,000. Preferred sources of protein include hydrolyzed animal protein such as available from Inolex as Lexein X250 and cocodimonium hydrolyzed animal protein available from Croda as Croquat M. Other protein sources that can be used include oat flour available from Quaker Oats as Oat Pro.

The present composition can be used to deliver an amount of moisturizer to the hair effective to provide body without adding a weighty oil coat to the hair. The moisturizing component is preferably from about 0.1-5.-% oif the composition. While the present composition may incorporate a number of common moisturizers such as Glycerin, Acetamide MEA or honey, the preferred moisturizer is hyaluronic acid, available from Diagnostics as Hyalure TN. It is believed that hyaluronic acid penetrates deeply into the hair and can be used in very small amounts. The present composition utilizes from about 0.000001-1% hyaluronic acid. While hyaluronic acid functions as a natural moisturizer, it may also bind to and carry the protein in the composition through the cuticle to the cortex of the hair to aid in reconstruction of the hair.

The present composition also incorporates a shine or sheen imparting component. Useful shine imparting components include henna extract, PVM/MA Copolymer, available from GAF Corporation as Gantrez AN169, PPG-5 Lanolin in ether available from Amerchol as Solulan PB-5 and Amodiomethicone available from Dow Corning as a component of Dow Corning 929 Emulsion. These shine imparting components may be used alone or in combination as is known by those of skill in the art. Preferred compositions include from about 0.5-20% of the shine imparting component. Most preferably, the shine imparting component includes from about 5-15% henna extract and 1-5% PVM/MA copolymer.

The present composition includes an oil phase that serves as a lubricating vehicle to enhance application. Useful oil phase compounds include fatty alcohols. The preferred oil phase components are fatty alcohols such as stearyl alcohol, and cetyl alcohol. The oil phase in the present composition preferably ranges from about 2-10%. More preferably, the oil phase is from about 3-7% fatty alcohol.

The aqueous phase of the present composition is preferably from about 20-60% water. More preferably, from about 20-40% water and most preferably from about 20-30% water. To eliminate the presence of undesired mineral impurities, deionized water is most preferred.

Nonionic emulsifiers are commonly added to the present composition to enhance solubilization of oil soluble components and fragrance. Preferably a combination of cationic and nonionic emulsifiers is used. Useful nonionic emulsifiers include nonoxynol surfactants such as available from Minnesota Solvents as Surfonic N-95. Preferred cationic emulsifiers include cetrimonium bromide, commercially available from Hexel as Bromat, tallowtrimonium chloride, available from Dow Corning 929 Emulsion, Quaternium 22, available from Van Dyke as Ceraphyl 60. In preferred compositions the cationic emulsifier component ranges from about 0.25-5%.

The present compositions can also include minor but effective amounts of various adjuvant materials including viscosity modifiers, preservatives and fragrances.

In the manufacture of the clay-based compositions the above-described components are mixed together in phases and in order consistant with available manufacturing equipment until a light modeling clay consistency is achieved. In order to avoid loss of malleability, the composition must be rapidly transferred to a storage container, such as a jar, before the composition further sets or gels.

In use the compositions of the present invention are preferably applied to hair after application of a chemical preparation such as a dye, bleach or permanent-waving preparation. Prior to application of the composition the hair is shampooed and excess water squeezed out. The composition is dispensed from its container and rubbed between the hands to enhance the liquidity and spreadability of the composition prior to application, thereby facilitating distribution of the composition in the hair. A liberal amount of the composition is applied to and worked into the hair and scalp. The treated hair is then exposed to heat for a period of time sufficient to dry the composition to a hard and flaky state. This is accomplished by exposing the hair to temperatures from about 80° F.-120° F. for a period of time between about 15-45 mintues.

Preferably, the treated hair is subjected to a two-step heat process. In the first step, the hair is enclosed in cover means such as a plastic cap or the like. The covered hair is heated for a period of time between about 13-30 minutes at a temperature from about 80° F.-120° F. under a preheated salon dryer of the type known in the art. Most preferably, the covered hair is heated for a period of time between about 20-30 mintues at a temperature of from about 90° F.-110° F. It is to be understood that by covering the hair with a cap the clay-based composition retains moisture for an extended period of time allowing the protein in the composition to bake into the hair thereby enhancing reconstruction of damaged hair. If hair dries too quickly, incorporation of protein into the hair is less complete. By covering the hair, protein incorporation is maximized.

The second step of the preferred heat treatment involves removing the cap and exposing the hair directly to heat at a temperature from about 80° F.-120° F. for a period of time between about 2-15 mintues. Most preferably, the second step of the heat treatment involves separating the hair with fingers and exposing the uncovered hair to a temperature of from about 90° F.-110° F. for a period of time between about 3-8 minutes. The head is then allowed to cool for several minutes. The application of heat to the exposed hair completes the drying of the composition, thereby polishing the hair and sealing the cuticle.

After the composition has dried to the desired hard and flaky state, it is removed by wetting the head with water and applying a cleansing shampoo of a type well known in the art.

The present composition will be further described by reference to the following detailed Example, and it is understood that the invention is not limited thereto. All parts are by weight unless other wise indicated.

EXAMPLE

The constituents below are blended in the weight percentages indicated to yield a paste composition.

| CTFA Designation | Trade Name | % by Weight |
|---|---|---|
| Deionized Water | Deionized Water | 24.81599 |
| Kaolin | Hydride | 18.13000 |
| Hydrolyzed Animal Protein | Lexein X250 | 12.00000 |
| Henna Extract | Henna Extract | 10.00000 |
| Amodimethicone (and) Nonoxynol-10 (and) Tallowtrimonium Chloride | Dow Corning 929 Emulsion | 8.00000 |
| Stearyl Alcohol | Stearyl Alcohol | 5.04900 |
| Fuller's Earth | Fuller's Earth | 4.41000 |
| PVM/MA Copolymer | Gantrez AN169 | 4.00000 |
| Glycerin | Glycerin | 3.00000 |
| Magnesium Aluminum silicate | Veegum HV | 2.64000 |
| Nonoxynol-10 | Surfonic N-95 | 0.25000 |
| Oat Flour | Oat Pro | 1.71500 |
| Acetamide MEA | Acetamide MEA | 1.50000 |
| Quaternium-22 | Ceraphyl 60 | 1.00000 |
| Hyaluronic Acid | Hyalure TN | 0.00001 |
| Cocodimonium Hydrolized Animal Protein | Croquat M | 0.50000 |
| PEG-5 Lanolin Ether | Solulan PB-5 | 0.50000 |
| Honey | Honey | 0.25000 |
| Cetrimonium Bromide | Bromat | 0.89100 |
| Cetyl Alcohol | Cetyl Alcohol | 0.42400 |
| Methylparaben | Methylparaben | 0.30000 |
| Propylparaben | Propylparaben | 0.07500 |
| DMDM Hydantoin | Glydant | 0.35000 |
| Gluteral | Ucarcide 225 | 0.20000 |
| Fragrance | Fragrance | Q.S |

What is claimed is:

1. A method for treating hair comprising the steps of:
   (a) applying an aqueous clay-based paste composition to hair; and
   (b) exposing the hair to heat for a period of time sufficient to completely dry the composition to a hard and flaky state, thereby maximizing the conditioning effect of the composition
   (c) shampooing the hair to remove the composition.

2. The method for treating hair according to claim 1 wherein the hair is exposed to heat for a period of time between about 15-45 minutes at a temperature of from about 80° F.-120° F.

3. A method for treating hair comprising the steps of:
   (a) applying an aqueous clay-based paste conditioning composition including a protein component to hair on an individual's head;
   (b) enclosing the hair in cover means;
   (c) exposing the hair to a temperature of from about 80° F.-120° F. for a period of time between 13-30 minutes, thereby allowing for maximum protein incorporation and hair reconstruction;
   (d) removing the cover means; and
   (e) exposing the hair to a temperature of from about 80° F.-120° F. for a period of time between about 2-15 minutes, thereby polishing the hair and sealing the cuticle.

4. The method of claim 3 wherein the hair in step (c) is exposed to a temperature of from about 90° F.-110° F. for a period of time between about 20-30 minutes and the hair in step (e) is exposed to a temperature of from about 90° F.-110° F. for a period of time between 3-8 minutes.

5. The method of claim 3 wherein said composition includes hyaluronic acid as a moisturizer.

6. The method of claim 3 wherein said aqueous based conditioning component includes from about 15-25% clay and from about 20-60% water.

7. The method of claim 6 wherein said aqueous clay-based conditioning component is a mixture of kaolin and fuller's earth.

* * * * *

UNITED STATES PATENT AND TRADEMARK OFFICE
CERTIFICATE OF CORRECTION

PATENT NO. : 5,002,076
DATED : March 26, 1991
INVENTOR(S) : Rocco F. Altobelli et al.

It is certified that error appears in the above-identified patent and that said Letters Patent is hereby corrected as shown below:

column 1, line 16, for "preparation" read --preparations-- column 2, line 26, after "present" insert --invention-- column 3, line 3, for "rhelogic" read --rheologic-- column 3, line 21, for "oif" read --of-- column 3, line 64, for "is" read --are-- column 5, line 25, for "PEG-5" read --PPG-5--

Signed and Sealed this

Twenty-eighth Day of December, 1993

Attest:

BRUCE LEHMAN

Attesting Officer

Commissioner of Patents and Trademarks